(12) United States Patent
Peng (10) Patent No.: US 9,958,431 B2
(45) Date of Patent: May 1, 2018

(54) ENDOTOXIN DETECTION SYSTEMS AND DETECTION METHODS THEREOF

(71) Applicant: NANJING TUOZHU PHARMACEUTICAL & TECH CO., LTD, Nanjing, Jiangsu (CN)

(72) Inventor: Guoping Peng, Jiangsu (CN)

(73) Assignee: Nanjing Tuozhu Pharmaceutical & Tech Co., Ltd., Nanjing (CN)

( * ) Notice: Subject to any disclaimer, the term of this patent is extended or adjusted under 35 U.S.C. 154(b) by 655 days.

(21) Appl. No.: 14/408,016

(22) PCT Filed: Jun. 13, 2013

(86) PCT No.: PCT/CN2013/077191
§ 371 (c)(1),
(2) Date: Dec. 15, 2014

(87) PCT Pub. No.: WO2013/185621
PCT Pub. Date: Dec. 19, 2013

(65) Prior Publication Data
US 2015/0106030 A1    Apr. 16, 2015

(30) Foreign Application Priority Data

May 14, 2012   (CN) .......................... 2012 1 0196596
Jun. 8, 2013   (CN) .......................... 2013 1 0228888

(51) Int. Cl.
*G01N 33/50*      (2006.01)
*G01N 21/47*      (2006.01)
(Continued)

(52) U.S. Cl.
CPC ......... *G01N 33/50* (2013.01); *G01N 15/0211* (2013.01); *G01N 21/47* (2013.01);
(Continued)

(58) Field of Classification Search
CPC .... G01N 15/0211; G01N 21/51; G01N 21/47; G01N 33/50; G01N 2015/0088;
(Continued)

(56) References Cited

U.S. PATENT DOCUMENTS

3,782,828 A * 1/1974 Alfano .................. G01J 3/2889
356/301
4,784,486 A * 11/1988 Van Wagenen ........... G01J 3/44
356/301
(Continued)

*Primary Examiner* — Sang Nguyen
(74) *Attorney, Agent, or Firm* — Ladas & Parry LLP (57) ABSTRACT

Endotoxin detection systems and corresponding detection methods integrate an optical path detection system based on a conventional laser particle size detector and detect the particle size distribution characteristics of the endotoxin colloidal particles in an aqueous solution by using laser light scattering. One system calculates the concentration of the endotoxin by fitting the correlation of the astigmatism with the concentration of the endotoxin based on scattering intensity of the endotoxin particles at more than three different angles via a quantitative operator. A second system tests the detection parameters of the concentration limits of a series of concentrations of endotoxin standard solutions by the laser light source intensity adjustment, the scanning mode adjustment and the detection parameter adjustment, then selects a corresponding detection parameter to test a sample, and determines whether the sample is satisfactory according to the range of particle size distribution peaks in the detection result.

9 Claims, 4 Drawing Sheets

(51) Int. Cl.
*G01N 21/51* (2006.01)
*G01N 15/02* (2006.01)
*G01N 15/00* (2006.01)

(52) U.S. Cl.
CPC ..... *G01N 21/51* (2013.01); *G01N 2015/0088* (2013.01); *G01N 2021/4711* (2013.01); *G01N 2201/06113* (2013.01)

(58) Field of Classification Search
CPC . G01N 2201/06113; G01N 2021/4711; G01N 21/64
See application file for complete search history.

(56) References Cited

U.S. PATENT DOCUMENTS

| | | | | |
|---|---|---|---|---|
| 5,185,265 A * | 2/1993 | Steen | ................ | G01N 15/1429 250/459.1 |
| 5,453,814 A * | 9/1995 | Aiyer | ................ | G03F 7/70208 355/53 |
| 5,872,627 A * | 2/1999 | Miers | ................ | G01N 15/1431 356/338 |
| 6,473,239 B1 * | 10/2002 | Volcker | ................ | G01N 21/253 250/486.1 |
| 6,646,742 B1 * | 11/2003 | Gangstead | ......... | G01N 15/1404 356/342 |
| 2008/0218738 A1 * | 9/2008 | Trainer | ................ | G01B 11/08 356/72 |
| 2009/0168064 A1 * | 7/2009 | Randow | .................... | G01J 3/02 356/434 |
| 2011/0284770 A1 * | 11/2011 | Nakada | ................ | G01N 15/147 250/459.1 |
| 2013/0183763 A1 * | 7/2013 | Obata | ................ | G01N 15/0205 436/94 |

\* cited by examiner

ENDOTOXIN DETECTION SYSTEMS AND DETECTION METHODS THEREOF

RELATED APPLICATION

This application is a national phase entry under 35 USC 371 of International Patent Application No PCT/CN/2013/077191 filed on 13 Jun. 2013, which was published on 19 Dec. 2013 with International Publication Number WO 2013/185621 A1, which claims priority from Chinese Patent Application No. 201210196596.8 filed on 14 Jun. 2012, and Chinese Patent Application No. 201310228888.X filed on 8 Jun. 2013, the disclosures of which are incorporated in their entirety by reference herein.

BACKGROUND OF THE INVENTION

Field of the Invention

The present invention relates to an endotoxin detection system on the basis of laser particle size detection and a corresponding detection method thereof, which fall within the field of detection of bacterial endotoxin.

Description of Related Art

Bacterial endotoxin is a lipopolysaccharide widely present in the nature, is also known as liposome and is a constituent in the external cell wall of Gram negative bacteria. After entering the blood circulation in human body, the substance may cause fever, that is, the commonly known pyrogenic reaction. Since the substance may cause serious adverse effects to human, its presence in pharmaceutical injections needs to be strictly controlled.

At present, the laser particle size detector has not found use in detection of endotoxin. As a high-sensitivity detector, the Malvern Nano ZS ZEW3600 laser particle size analyzer is shown to detect the particles of endotoxin in a solution only at a concentration above 10 EU/ml, which fails to satisfy the requirements for endotoxin detection in injections. The particle size analysis by the laser particle size detector is performed with multi-point scattered light signals from more than two points based on differences in scattered light signals from the particles at different angles. However, the laser particle size detector is still not applicable to detection of particle concentration.

The detection of bacterial endotoxin may be either qualitative or quantitative. A conventional detection method uses rabbit, where a test sample is intravenously injected into rabbit, and changes in body temperature are observed for a specified period of time. The method may be subjected to interference from many factors, poor sensitivity, and especially potential occurrence of false negative results for antipyretic drugs or heat-clearing and detoxicating injections. In the pharmacopoeia of People's Republic of China, tachypleus amebocyte lysate (TAL) test is used for detection of endotoxin; however, the method has the disadvantages of long preparation time, extended detection time, and high cost, and rapid, continuous, and on-line detection cannot be realized therewith.

SUMMARY OF THE INVENTION

In view of the disadvantages existing in the prior art, the present invention provides two endotoxin detection systems and corresponding detection methods thereof, to reduce the detection cost and increase the detection speed.

A first endotoxin detection system includes a laser source, a short focal length lens, a grating, a long focal length lens, a detection cell, a scattered light receiver, a photoelectric converter, a signal amplifier, a signal processor, a data collector, a quantitative operator, and a data display. Light output from the laser source passes sequentially through the short focal length lens, the grating, and the long focal length lens, and then into the detection cell. Transmitted light from the detection cell is received by the scattered light receiver, and then enters the photoelectric converter. A signal output from the photoelectric converter is passed sequentially to the signal amplifier, the signal processor, and the data collector, and then to the quantitative operator for calculating the endotoxin concentration. The quantitative operator has an output connected to the data display.

A detection method on the basis of the first endotoxin detection system comprises the following.

The scattered light signal intensity of the endotoxin particles in a solution is detected at more than three different angles, and according to the light scattering formula $I=K \cdot C \cdot f(D) \cdot f(E)$, $f(D)$ and $f(E)$ are calculated from the scattered light signals at any two of the angles. Accordingly, the light scattering formula is simplified as $S=f \cdot C+g$. Then, the endotoxin concentration in the solution is calculated with the scattered light signals at the rest angles, thereby realizing quantitative detection.

In the formula above, $I$ is a scattered light signal intensity; $K$ is a proportional constant; $C$ is a endotoxin concentration; $f(D)$ is a function of particle size parameter; $f(E)$ is a scattering function; $S$ is light scattering degree, and $S$ is obtained by ln linearization processing of $I$; the correlation coefficient $f=K \cdot f(D) \cdot f(E)$; and $g$ is a correction parameter.

A second endotoxin detection system includes a laser source, a light intensity regulator, a scanning mode regulator, a short focal length lens, a grating, a long focal length lens, a detection cell, a scattered light receiver, a photoelectric converter, a signal amplifier, a signal processor, a data collector, a quasi-quantitative operator, and a data display. Light output from the laser source passes sequentially through the short focal length lens, the grating, and the long focal length lens, and then into the detection cell. Transmitted light from the detection cell is received by the scattered light receiver, and then enters the photoelectric converter. A signal output from the photoelectric converter is passed sequentially to the signal amplifier, the signal processor, and the data collector, and then to the quasi-quantitative operator for detecting the concentration limits of endotoxin. All of the signal amplifier, the signal processor, the data collector, and the quasi-quantitative operator have an output connected via the light intensity regulator to the laser source, and the output of the quasi-quantitative operator is also connected via the scanning mode regulator to the laser source. The data display is connected to the output of the quasi-quantitative operator.

A detection method on the basis of the second endotoxin detection system includes a polydisperse particle size distribution detection and a monodisperse particle size distribution detection.

The polydisperse particle size distribution detection includes the following steps.

Step 1-1: adjust the intensity of the laser source;

Step 1-2: adjust the scanning mode regulator, and set the laser source in a step scan mode;

Step 1-3: prepare a series of concentrations of standard endotoxin solutions, and conduct polydisperse particle size distribution detection on each concentration of the standard endotoxin solution;

Step 1-4: detect the concentration limits of each concentration of the standard endotoxin solution by setting the detection parameters in the quasi-quantitative operator; and Step 1-5: conduct polydisperse particle size distribution detection on a sample by setting the detection parameters in the quasi-quantitative operator as desired by the sample, where when the detection result shows that no particle size distribution peak of endotoxin appears in the range of 20-300 nm, the concentration of endotoxin in the sample is below the corresponding concentration limit, or otherwise, the concentration of endotoxin in the sample is above the corresponding concentration limit.

The monodisperse particle size distribution detection includes the following steps.

Step 2-1: adjust the intensity of the laser source;

Step 2-2: adjust the scanning mode regulator, and set the laser source in a full scan mode;

Step 2-3: prepare a series of concentrations of standard endotoxin solutions, and conduct monodisperse particle size distribution detection on each concentration of the standard endotoxin solution;

Step 2-4: detect the concentration limits of each concentration of the standard endotoxin solution by setting the detection parameters in the quasi-quantitative operator; and Step 2-5: conduct monodisperse particle size distribution detection on a sample by setting the detection parameters in the quasi-quantitative operator as desired by the sample, where when the detection result shows that the particle size distribution peak of endotoxin appears below 20 nm, the concentration of endotoxin in the sample is below the corresponding concentration limit, or otherwise, the concentration of endotoxin in the sample is above the corresponding concentration limit.

Technical Effects:

1. The cost for endotoxin detection is greatly reduced since no reagent (tachypleus amebocyte lysate) is consumed.

2. The optical path systems are integrated to improve the detection sensitivity, thus being applicable in detection of endotoxin above 0.5 EU/ml in a solution.

3. The detection modes include on-line and off-line modes, thus being flexible in application and having a good utility.

4. The detection time of endotoxin is greatly reduced to realize fast detection, thus being useful for fast detection and determination of endotoxin limits in water for injection, semi-finished injection products, and finished injection products.

5. An early warning system is added, which alarms in the case that the concentration of endotoxin in a solution is out of limits, thereby achieving on-line monitoring with high reliability.

Figure 1:
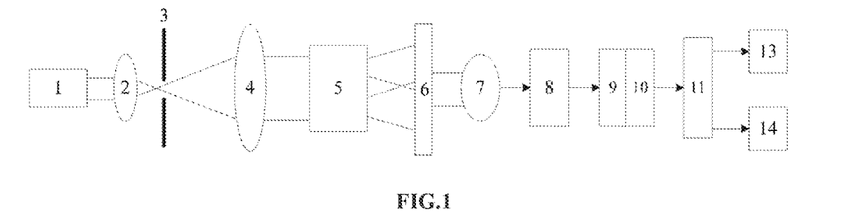
FIG. 1 is a block diagram showing the structure of a first endotoxin detection system according to the present invention.
Figure 4:
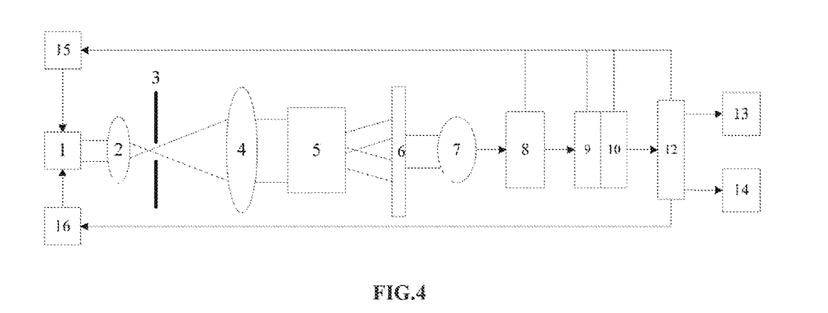
FIG. 4 is a block diagram showing the structure of a second endotoxin detection system according to the present invention.

List of reference numerals in FIGS. 1 and 4: 1. Laser source; 2. Short focal length lens; 3. Grating; 4. Long focal length lens; 5. Detection cell; 6. Scattered light receiver; 7. Photoelectric converter; 8. Signal amplifier; 9. Signal processor; 10. Data collector; 11. Quantitative operator; 12, Quasi-quantitative operator, 13. Data display; 14. Early warning means; 15. Light intensity regulator; 16. Scanning mode regulator.

DETAILED DESCRIPTION OF THE INVENTION (I) First Endotoxin Detection System

A first endotoxin detection system according to the present invention has a structure as shown in FIG. 1, and includes a laser source 1, a short focal length lens 2, a grating 3, a long focal length lens 4, a detection cell 5, a scattered light receiver 6, a photoelectric converter 7, a signal amplifier 8, a signal processor 9, a data collector 10, a quantitative operator 11, and a data display 13. Light output from the laser source 1 passes sequentially through the short focal length lens 2, the grating 3 and the long focal length lens 4, and then into the detection cell 5. Transmitted light from the detection cell 5 is received by the scattered light receiver 6, and then enters the photoelectric converter 7. A signal output from the photoelectric converter 7 is passed sequentially to the signal amplifier 8, the signal processor 9 and the data collector 10, and then to the quantitative operator 11 for calculating the endotoxin concentration. The quantitative operator 11 has an output connected to the data display 13.

Figure 2:
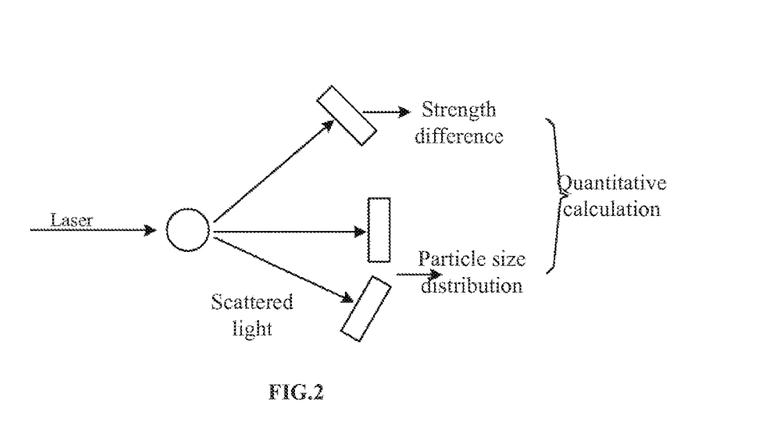
FIG. 2 is a schematic diagram showing the principle for quantitative calculation of endotoxin.
Figure 3:
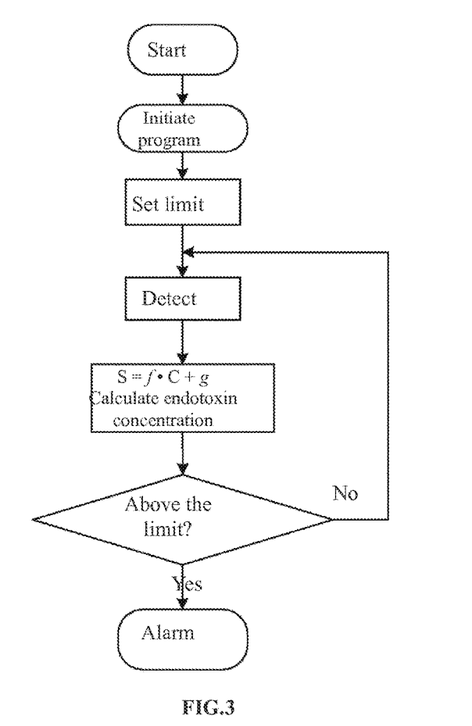
FIG. 3 is a flow chart of detection and early warning by the first endotoxin detection system according to the present invention.

The endotoxin detection system is to integrate an optical path detection system on the basis of a conventional laser particle size detector and preferably used for detection in a scattered light path at about 90 degree. The laser source 1 is the FLS-2600B dual-beam laser source available from EXFO Inc., Canada. The short focal length lens 2 is an ultra-low dispersive lens. The grating 3 is a fiber grating of fiber coupler type. The long focal length lens 4 is a low-loss NV-202m lens. The detection cell 5 is made of optical glass, and includes an on-line detection cell and an off-line detection cell. The on-line detection cell has a liquid outlet and inlet disposed at top and bottom ends thereof, respectively, and connected in the pipeline of an injection production line through the liquid outlet and inlet to form a loop, thereby realizing continuous detection of drug injections. An electromagnetic valve is disposed respectively on the liquid outlet and inlet, and an ultrasonic probe is further disposed on the liquid inlet, for eliminating the interferences from bubbles. The off-line detection cell is a semi-tight, removable detection cell, and has a liquid filling port disposed at a top end thereof, for manually replacing the solution therein. The scattered light receiver 6 is a Picometrix LLC high-speed, multi-point, wide-angle scattered light receiver module available from API Corporation, employing logarithmic arrangement with multi-point interval. The photoelectric converter 7 is a HESMC photoelectric converter available from Henqi Electronics Co., Ltd, America. The signal amplifier 8 consists of an amplifier circuit and a filter circuit, in which the amplifier circuit is a differential amplification circuit formed by connecting three ICL7650 amplifiers, and the filter is a commonly used RC network. The signal processor 9 is a CONVERTER-VLC.602 programmable signal processor available from VAL.CO, Italian. The data collector 10 is an A/D converter Maxl32 available from Maxim Integrated. The calculation principle of the quantitative operator 11 is as shown in FIG. 2. According to the light scattering formula $I=K \cdot b \cdot C \cdot f(D) \cdot f(E) \cdot f(\Delta\lambda)$, where I is a scattered light signal intensity, K is a proportional constant, b is the thickness of a solution to be tested, C is endotoxin concentration (in EU/ml), f(D) is a function of particle size parameter, f(E) is a scattering function, and $f(\Delta\lambda)$ is a function of wavelength, since the thickness of the solution to be tested (colorimetric cell) and the wavelength are fixed, b and $f(\Delta\lambda)$ are constant. Accordingly, the light scattering formula may be simplified as $I=K \cdot C \cdot f(D) \cdot f(E)$. The constant K can be calculated by detecting with different concentrations of standard endotoxin solutions. The scattered light signal intensity of the endotoxin particles in a solution is detected by the system at more than three different angles, and according to the formula $I=K \cdot C \cdot f(D) \cdot f(E)$, f(D) and f(E) are calculated from the scattered light signals at any two of the angles. Accordingly, the light scattering formula is simplified as $S=f \cdot C+g$, where S is a light scattering degree, and S is obtained by ln linearization processing of I; the correlation coefficient $f=K \cdot f(D) \cdot f(E)$; and g is a correction parameter. Then, the endotoxin concentration in the solution is calculated with the scattered light signals at the rest angles, thereby realizing quantitative detection. The data display 13 is a 128×64 dot-matrix display terminal available from Jinchuangdao Co., Ltd, used for displaying the detected concentration value of the endotoxin. To have an early warning function, the present system is further provided with an early warning means 14 connected to the quantitative operator 11. The early warning means 14 employs the CMS7000-500 alarming and monitoring software available from Chengjiu Electronics Co. Ltd. and a piezoelectric early warning system integrated. The detection early warning process of the present system is as shown in FIG. 3. A concentration limit of endotoxin may be preset in the early warning software, and the alarming indicator alarms when the concentration of endotoxin in the solution detected is above the limit.

The process for on-line detection by the first endotoxin detection system according to the present invention is as follows. As desired in production, a concentration limit of endotoxin, the coefficient f and the parameter g are preset in the quantitative operator, and then the production line is initiated to allow a solution to enter the on-line detection cell. According to the formula $S=f \cdot C+g$, the concentration of endotoxin is calculated, where the concentration is below the limit, the system continues to operate, and where the concentration is above the limit, the early warning system alarms.

The operation steps in off-line detection by the first endotoxin detection system according to the present invention are as follows. The coefficient f and the parameter g are preset in the quantitative operator. The off-line detection cell is removed and washed with purified water, and then ultrasonically washed 2-3 times with the test solution. The test solution is added, and the detection cell is placed in the present system. According to the formula $S=f \cdot C+g$, the concentration of endotoxin is calculated.

An example for off-line quantitative detection of endotoxin in a Dan-shen drop infusion solution by the first endotoxin detection system is given hereinafter.

The off-line detection cell was replaced. The control standard endotoxin was formulated into a 100 EU/ml standard endotoxin solution with water for detection, which was then serially diluted with the water for detection into standard endotoxin solutions with a concentration of 0.5, 1, 5, 10, and 50 EU/ml respectively. The solution was placed in the detection cell for detection. Regression analysis was performed by the quantitative operator, and the linear equation was $S=0.056C+0.165$, $R^2=0.997$. The calculation results are shown in Table 1.

TABLE 1

| Endotoxin concentration (EU/ml) | Light scattering degree |
|---|---|
| 0.5 | 0.107 |
| 1 | 0.217 |
| 5 | 0.523 |
| 10 | 0.761 |
| 50 | 2.988 |

The concentration of endotoxin in an intermediate Dan-shen drop infusion solution (available from Shanghai Huayuan Anhui Jinhui Pharmaceutical Co., Ltd, Lot number: 05110209) was respectively detected by the present system and the turbidity assay with TAL. The results are shown in Table 2.

TABLE 2

| Detection method | Concentration | Detection time |
|---|---|---|
| Present system | 23.3 EU/ml | 3 min |
| Turbidity assay with TAL | 22.8 EU/ml | 35 min |

The results show that the endotoxin content detected by the present system is approximate to that detected by the turbidity assay with TAL. At present, the turbidity assay with TAL is a method documented in the Pharmacopoeia of People's Republic of China, and the detection results obtained therefrom are accurate. The approximation of the results detected by the present system thereto indicates the reliability of the present system.

An example for on-line quantitative detection of endotoxin in a Dan-shen drop infusion solution by the first endotoxin detection system is given hereinafter.

On-line detection was respectively performed on a normal Dan-shen drop infusion solution (available from Shanghai Huayuan Anhui Jinhui Pharmaceutical Co., Ltd, Lot number: 10011605), and a contaminated Dan-shen drop infusion solution. The detection parameters were set as follows: f=0.056, g=0.165, and endotoxin limit=1 EU/mL. Then the production line is initiated for detection. The concentration of endotoxin was calculated according to the regression equation $S=0.056C+0.165$. The results are shown in Table 3.

TABLE 3

| Sample of Dan-shen drop infusion solution | Endotoxin concentration (EU/ml) | Sysem status |
|---|---|---|
| Normal | Below limit | Normal |
| Contaminated | 50.2 | Alarm |

The results show that when the endotoxin contaminant is above the limit, the present system alarms, thereby realizing quantitative monitoring of the contamination status caused by endotoxin in the production of injections.

(II) Second Endotoxin Detection System

A second endotoxin detection system according to the present invention has a structure as shown in FIG. 4, and includes a laser source 1, a short focal length lens 2, a grating 3, a long focal length lens 4, a detection cell 5, a scattered light receiver 6, a photoelectric converter 7, a signal amplifier 8, a signal processor 9, a data collector 10, a quasi-quantitative operator 12, a data display 13, a light intensity regulator 15, and a scan mode regulator 16. Light output from the laser source 1 passes sequentially through the short focal length lens 2, the grating 3 and the long focal length lens 4, and then into the detection cell 5. Transmitted light from the detection cell 5 is received by the scattered light receiver 6 and then enters the photoelectric converter 7. A signal output from the photoelectric converter 1 is passed sequentially to the signal amplifier 8, the signal processor 9 and the data collector 10, and then to the quasi-quantitative operator 12 for detecting the concentration limits of endotoxin. All of the signal amplifier 8, the signal processor 9, the data collector 10, and the quasi-quantitative operator 12 have an output connected via the light intensity regulator 15 to the laser source 1, and the output of the quasi-quantitative operator 12 is also connected via the scanning mode regulator 16 to the laser source 1. The data display 13 is connected to the output of the quasi-quantitative operator 12.

Likewise, the endotoxin detection system is preferably used for detection in a scattered light path at about 90 degree. The laser source 1 is a mono- or dual-beam laser source, and the FLS-2600B dual-beam laser source available from EXFO Inc., Canada is again used herein. The light intensity regulator 15 is the AVR-8A energy regulator available from Bokang Co., Ltd, America, used for regulating the strength of the laser source 1. The scan mode regulator 16 is used for controlling the scan range of particle size, and can operate in a step scan mode and a full scan mode. The scan range of the step scan mode is 1-10 nm (preferably 1-5 nm), 5-500 nm (preferably 5-200 nm), and 100-1000 nm (preferably 200-1000 nm), and the scan range of the full scan mode is 1-1000 nm. The quasi-quantitative operator 13 integratedly stores detection parameters for different endotoxin concentration detection sensitivities (concentration limits), including detection parameters for concentration limits of 0.5 EU/ml and natural numbers between 1-10 (EU/ml). The selection of different detection limits may be made according to the limit requirements for endotoxin content in different samples. The detection parameters include a magnification factor, a channel number, a delay coefficient, and a speed coefficient. The short focal length lens 2, the grating 3, the long focal length lens 4, the detection cell 5, the scattered light receiver 6, the photoelectric converter 7, the signal amplifier 8, the signal processor 9, the data collector 10 and the data display 13 are the same as those in the first endotoxin detection system. To have an early warning function, the second endotoxin detection system is also provided with an early warning means 14 connected to the output of the quasi-quantitative operator 12. The early warning means 14 is the same as that in the first endotoxin detection system.

A detection method on the basis of the second endotoxin detection system includes a polydisperse particle size distribution detection and a monodisperse particle size distribution detection.

The polydisperse particle size distribution detection includes the following steps.

Step 1-1: adjust the intensity of the laser source;
Step 1-2: adjust the scanning mode regulator, and set the laser source in a step scan mode;
Step 1-3: prepare a series of concentrations of standard endotoxin solutions, and conduct polydisperse particle size distribution detection on each concentration of the standard endotoxin solution;
Step 1-4: detect the concentration limits of each concentration of the standard endotoxin solution by setting the detection parameters in the quasi-quantitative operator; and
Step 1-5: conduct polydisperse particle size distribution detection on a sample by setting the detection parameters (that is, selecting detection sensitivity) in the quasi-quantitative operator according to the limit requirement for endotoxin content in the sample, where when the detection result shows that no particle size distribution peak of endotoxin appears in the range of 20-300 nm, the concentration of endotoxin in the sample is below the corresponding concentration limit, that is, acceptable, or otherwise, the concentration of endotoxin in the sample is above the corresponding concentration limit, that is, unacceptable.

The monodisperse particle size distribution detection includes the following steps.

Step 2-1: adjust the intensity of the laser source;
Step 2-2: adjust the scanning mode regulator, and set the laser source in a full scan mode;
Step 2-3: prepare a series of concentrations of standard endotoxin solutions, and conduct monodisperse particle size distribution detection on each concentration of the standard endotoxin solution;
Step 2-4: detect the concentration limits of each concentration of the standard endotoxin solution by setting the detection parameters in the quasi-quantitative operator; and
Step 2-5: conduct monodisperse particle size distribution detection on a sample by setting the detection parameters (that is, selecting detection sensitivity) in the quasi-quantitative operator according to the limit requirement for endotoxin content in the sample, where when the detection result shows that the particle size distribution peak of endotoxin appears below 20 nm, the concentration of endotoxin in the sample is below the corresponding concentration limit, that is, acceptable, or otherwise, the concentration of endotoxin in the sample is above the corresponding concentration limit, that is, unacceptable.

Detection examples using the second endotoxin detection system are given hereinafter.

Acquisition of Parameters in the Quasi-Quantitative Operator:

Instruments and materials: a. CN-11 nano particle size analyzer for endotoxin solution; b. control standard bacterial endotoxin (lot number: 150601-201176, specification: 100 EU-Amp1, National Institutes for Food and Drug Control); c. water for detection of bacterial endotoxin (lot number: 100130, Zhanjiang Bokang Ocean Creature Co., Ltd.).

Method: The control standard endotoxin was formulated into a 100 EU/ml standard endotoxin solution with water for detection, which was then serially diluted with the water for detection into standard endotoxin solutions with a concentration of 10.0 EU/ml, 5.0 EU/ml, 2.0 EU/ml, 1.0 EU/ml and 0.5 EU/ml respectively.

The CN-11 nano particle size analyzer for endotoxin solution was started and preheated for over 30 min. The series of standard endotoxin solutions from low to high level were sequentially added to the detection cell for detection. The detection parameters (a magnification factor, a channel number, a delay coefficient, and a speed coefficient) were set, and the detection sensitivity of the nano particle size analyzer was adjusted. Preferred detection parameters are as shown in 4, which was stored in the quasi-quantitative operator.

TABLE 4

| Endotoxin concentration | Light intensity | Magnification factor | Channel number | Delay coefficient | Speed coefficient |
|---|---|---|---|---|---|
| 0.5 EU/ml | 100 | 500 | 400 | 50 | 30 |
| 1.0 EU/ml | 90 | 400 | 350 | 60 | 40 |
| 2.0 EU/ml | 80 | 300 | 300 | 60 | 45 |
| 5.0 EU/ml | 65 | 200 | 300 | 70 | 35 |
| 10.0 EU/ml | 50 | 200 | 200 | 90 | 60 |

I. Detection of Endotoxin Content in an Intermediate Dan-Shen Drop Infusion Solution with Polydisperse Particle Size Distribution Detection and Dynamic Turbidity Assay Respectively Instruments and materials: a. CN-11 nano particle size analyzer for endotoxin solution; b. BET-16M bacterial endotoxin tester; c. TAL for dynamic turbidity assay (lot number: 1303270, $\lambda=0.03$ EU·mL$^{-1}$, specification: 0.6 mL·Amp$^{-1}$, Zhanjiang Bokang Ocean Creature Co., Ltd.); d. control standard bacterial endotoxin (150601-201176, specification: 100 EU·Amp$^{-1}$, National Institutes for Food and Drug Control); e. water for detection of bacterial endotoxin (lot number: 070130, specification: 5 mL·Amp$^{-1}$, Zhanjiang Bokang Ocean Creature Co., Ltd.); f. bacterial endotoxin indicator (lot number: 071114, specification: 3000 EU·Amp$^{-1}$, Zhanjiang Bokang Ocean Creature Co., Ltd.); g. intermediate Dan-shen drop infusion solution (lot number: 201302191, Shanghai Huayuan Anhui Jinhui Pharmaceutical Co., Ltd).

Figure 5:
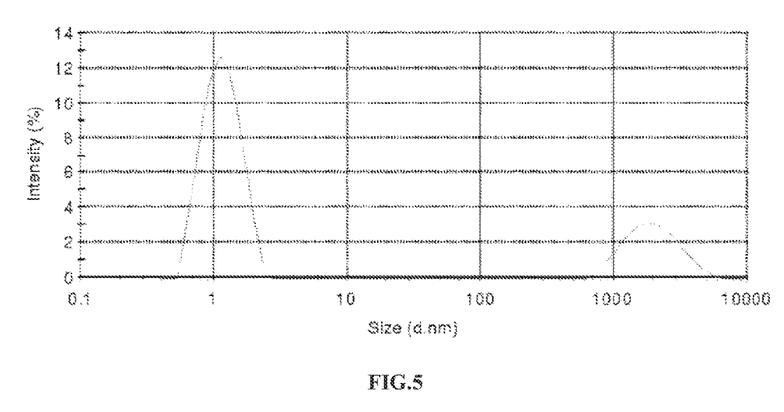
FIG. 5 shows detection results of endotoxin in a polydisperse particle size distribution detection example using a detection parameter set to 5.0 EU/ml.
Figure 6:
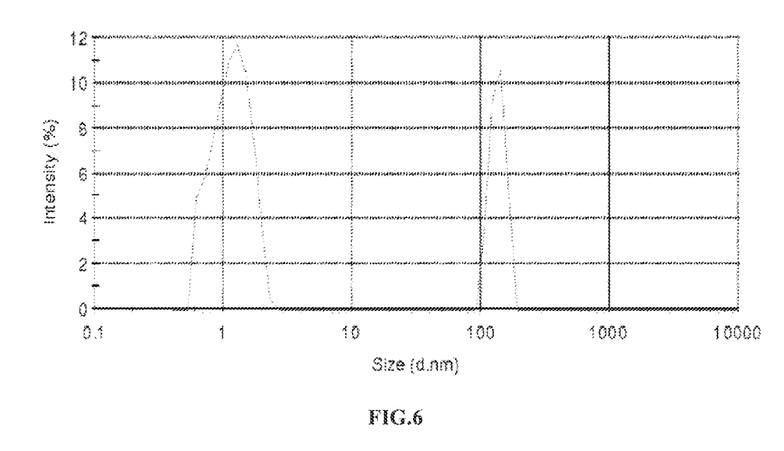
FIG. 6 shows detection results of endotoxin in a polydisperse particle size distribution detection example using a detection parameter set to 2.0 EU/ml.

Method: the polydistribution detection was performed on the intermediate Dan-shen drop infusion solution in a step scan mode according to the limit requirement for endotoxin content in the intermediate Dan-shen drop infusion solution. The endotoxin content was detected with the detection limit parameter set to 5.0 EU/ml and 2.0 EU/ml and also using turbidity assay with TAL. The results are shown in FIG. 5, FIG. 6, and Table 5.

TABLE 5

| Detection method | Endotoxin content |
|---|---|
| Turbidity assay with TAL | 2.8 EU/ml |

The results show that the sample is detected to be unacceptable with the detection limit parameter set to 2.0 EU/ml, and detected to be acceptable with the detection limit parameter set to 5.0 EU/ml, suggesting that endotoxin concentration in the sample is below 5.0 EU/ml and above 2.0 EU/ml, which is in accord with the test result from the turbidity assay with TAL, thus validating the reliability of the present method.

Figure 7:
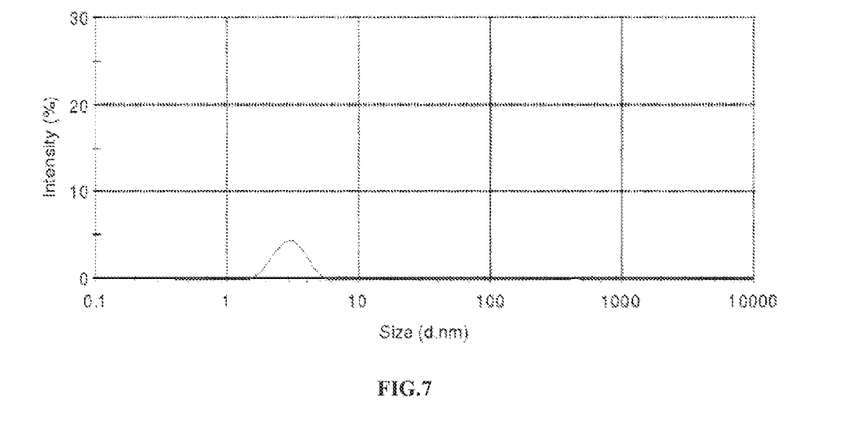
FIG. 7 shows detection results of endotoxin in a monodisperse particle size distribution detection example using a detection parameter set to 10.0 EU/ml.
Figure 8:
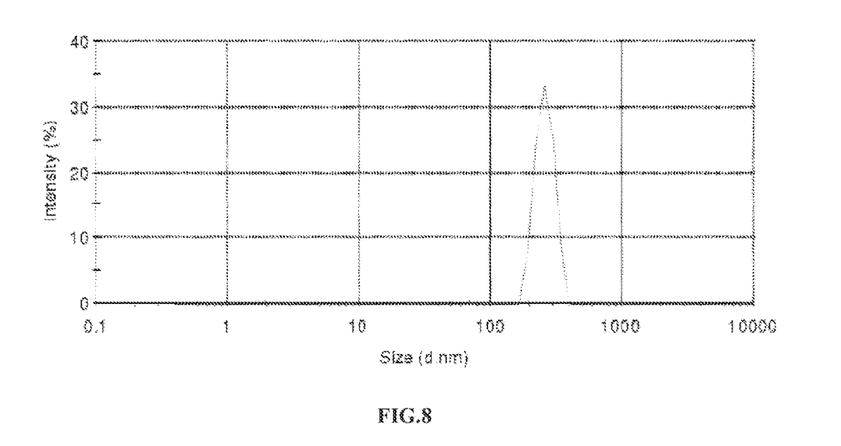
FIG. 8 shows detection results of endotoxin in a monodisperse particle size distribution detection example using a detection parameter set to 7.0 EU/ml.

II. Detection of Endotoxin Content in an Intermediate Xiaoaiping Injection with Monodisperse Particle Size Distribution Detection and Dynamic Turbidity Assay Respectively The monodistribution detection was performed on the intermediate Xiaoaiping injection in a full scan mode according to the limit requirement for endotoxin content in the intermediate Xiaoaiping injection. The endotoxin content was scanned with the detection limit parameter set to 10.0 EU/ml. The result is as shown in FIG. 7, showing that no particle size distribution peak appears above 20 nm. After additionally adding standard endotoxin, the endotoxin content was detected to be 8.0 EU/ml through dynamic turbidity assay with TAL. Thus, the detection was further conducted with the detection limit parameter set to 7.0 EU/ml. The result is shown in FIG. 8, showing that the particle size distribution peak is shifted to 270 nm, which suggests that the endotoxin content in the sample is above the limit 7.0 EU/ml, which is in accord with the test result from turbidity assay with TAL, thus further validating the reliability of the present method.

What is claimed is:

1. An endotoxin detection system, comprising a laser source, a short focal length lens, a grating, a long focal length lens, a detection cell, a scattered light receiver, a photoelectric converter, a signal amplifier, a signal processor, a data collector, a quantitative operator, and a data display, wherein light output from the laser source passes sequentially through the short focal length lens, the grating, and the long focal length lens, and then into the detection cell; transmitted light from the detection cell is received by the scattered light receiver, and then enters the photoelectric converter; and a signal output from the photoelectric converter is passed sequentially to the signal amplifier, the signal processor, and the data collector, and then to the quantitative operator for calculating the endotoxin concentration, the quantitative operator having an output connected to the data display wherein the scattered light receiver is configured to detect signal intensity of the endotoxin particles in a solution at more than three different detection angles, and the quantitative operator is configured to calculate f(D) and f(E) according to the light scattering formula I=K·C·f(D)·f(E) from the scattered light signals at any two of the angles, simplifying the light scattering formula as S=f·C+g, and calculating the endotoxin concentration in the solution with the scattered light signals at the rest angles, thereby realizing quantitative detection;

wherein in the formula above, I is a scattered light signal intensity; K is a proportional constant; C is an endotoxin concentration; f(D) is a function of particle size parameter; f(E) is a scattering function; S is a light scattering degree, and S is obtained by ln linearization processing of I; the correlation coefficient f=K·f(D)·f(E); and g is a correction parameter.

2. The endotoxin detection system according to claim 1, further comprising an early warning means connected to the output of the quantitative operator.

3. The endotoxin detection system according to claim 1, wherein the detection cell is made of optical glass and includes an on-line detection cell and an off-line detection cell.

4. An endotoxin detection system, comprising a laser source, a light intensity regulator, a scanning mode regulator, a short focal length lens, a grating, a long focal length lens, a detection cell, a scattered light receiver, a photoelectric converter, a signal amplifier, a signal processor, a data collector, a quasi-quantitative operator, and a data display, wherein light output from the laser source passes sequentially through the short focal length lens, the grating, and the long focal length lens, and then into the detection cell; transmitted light from the detection cell is received by the scattered light receiver, and then enters the photoelectric converter; and a signal output from the photoelectric converter is passed sequentially to the signal amplifier, the signal processor, and the data collector, and then to the quasi-quantitative operator for detecting the concentration limits of endotoxin; and wherein all of the signal amplifier, the signal processor, the data collector, and the quasi-quantitative operator have an output connected via the light intensity regulator to the laser source, the output of the quasi-quantitative operator is also connected via the scanning mode regulator to the laser source, and the data display is connected to the output of the quasi-quantitative operator.

5. The endotoxin detection system according to claim 4, further comprising an early warning means connected to the output of the quasi-quantitative operator.

6. The endotoxin detection system according to claim 4, wherein the scanning mode regulator is operable in a step scan mode and a full scan mode, the scan range of the step scan mode being 1-10 nm, 5-500 nm, and 100-1000 nm, and the scan range of the full scan mode being 1-1000 nm.

7. The endotoxin detection system according to claim 4, wherein the detection cell is made of optical glass and includes an on-line detection cell and an off-line detection cell.

8. An endotoxin detection method comprising a polydisperse particle size distribution detection and a monodisperse particle size distribution detection utilizing a system comprising a laser source, a light intensity regulator, a scanning mode regulator, a short focal length lens, a grating, a long focal length lens, a detection cell, a scattered light receiver, a photoelectric converter, a signal amplifier, a signal processor, a data collector, a quasi-quantitative operator, and a data display, wherein light output from the laser source passes sequentially through the short focal length lens, the grating, and the long focal length lens, and then into the detection cell; transmitted light from the detection cell is received by the scattered light receiver, and then enters the photoelectric converter; and a signal output from the photoelectric converter is passed sequentially to the signal amplifier, the signal processor, and the data collector, and then to the quasi-quantitative operator for detecting the concentration limits of endotoxin; and wherein all of the signal amplifier, the signal processor, the data collector, and the quasi-quantitative operator have an output connected via the light intensity regulator to the laser source, the output of the quasi-quantitative operator is also connected via the scanning mode regulator to the laser source, and the data display is connected to the output of the quasi-quantitative operator , wherein the polydisperse particle size distribution detection comprises:

Step 1-1: adjusting the intensity of the laser source;
Step 1-2: adjusting the scanning mode regulator, and setting the laser source in a step scan mode;
Step 1-3: preparing a series of concentrations of standard endotoxin solutions, and conducting polydisperse particle size distribution detection on each concentration of the standard endotoxin solution;
Step 1-4: detecting the concentration limits of each concentration of the standard endotoxin solution by setting the detection parameters in the quasi-quantitative operator; and
Step 1-5: conducting polydisperse particle size distribution detection on a sample by setting the detection parameters in the quasi-quantitative operator as desired by the sample, wherein when the detection result shows that no particle size distribution peak of endotoxin appears in the range of 20-300 nm, the concentration of endotoxin in the sample is below the corresponding concentration limit, or otherwise, the concentration of endotoxin in the sample is above the corresponding concentration limit; and the monodisperse particle size distribution detection comprises:
Step 2-1: adjusting the intensity of the laser source;
Step 2-2: adjusting the scanning mode regulator, and setting the laser source in a full scan mode;
Step 2-3: preparing a series of concentrations of standard endotoxin solutions, and conducting monodisperse particle size distribution detection on each concentration of the standard endotoxin solution;
Step 2-4: detecting the concentration limits of each concentration of the standard endotoxin solution by setting the detection parameters in the quasi-quantitative operator; and
Step 2-5: conducting monodisperse particle size distribution detection on a sample by setting the detection parameters in the quasi-quantitative operator as desired by the sample, wherein when the detection result shows that the particle size distribution peak of endotoxin appears below 20 nm, the concentration of endotoxin in the sample is below the corresponding concentration limit, or otherwise, the concentration of endotoxin in the sample is above the corresponding concentration limit.

9. The detection method on the basis of the endotoxin detection system according to claim 8, wherein the detection parameters set in the quasi-quantitative operator comprises a magnification factor, a channel number, a delay coefficient, and a speed coefficient.

* * * * *